(12) United States Patent
Gilkerson et al.

(10) Patent No.: US 8,494,634 B2
(45) Date of Patent: *Jul. 23, 2013

(54) VECTOR CONFIGURATION DETECTION AND CORRECTIVE RESPONSE SYSTEMS AND METHODS

(75) Inventors: James O. Gilkerson, Stillwater, MN (US); David L. Perschbacher, Coon Rapids, MN (US); James Kalgren, Lino Lakes, MN (US); Les N. Peterson, Woodbury, MN (US); Mitchell Lanz, Maple Grove, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 13/476,651

(22) Filed: May 21, 2012

(65) Prior Publication Data

US 2012/0296385 A1 Nov. 22, 2012

Related U.S. Application Data

(63) Continuation of application No. 12/333,165, filed on Dec. 11, 2008, now Pat. No. 8,185,203.

(60) Provisional application No. 61/007,836, filed on Dec. 14, 2007.

(51) Int. Cl.
*A61N 1/00* (2006.01)
(52) U.S. Cl.
USPC .......................................................... 607/30
(58) Field of Classification Search
USPC ..................................... 607/9, 27–30, 59, 60
See application file for complete search history.

(56) References Cited

U.S. PATENT DOCUMENTS

| 4,964,407 | A | 10/1990 | Baker, Jr. et al. |
| 5,003,975 | A | 4/1991 | Hafelfinger et al. |
| 5,431,692 | A | 7/1995 | Hansen et al. |
| 5,534,018 | A | 7/1996 | Wahlstrand et al. |
| 5,755,742 | A | 5/1998 | Schuelke et al. |
| 5,814,088 | A | 9/1998 | Paul et al. |
| 6,317,633 | B1 | 11/2001 | Jorgenson et al. |
| 6,516,227 | B1 | 2/2003 | Meadows et al. |
| 6,782,291 | B1 | 8/2004 | Bornzin et al. |
| 6,978,171 | B2 | 12/2005 | Sommer et al. |
| 6,978,178 | B2 | 12/2005 | Goetz et al. |
| 7,047,083 | B2 | 5/2006 | Gunderson et al. |
| 8,185,203 | B2 | 5/2012 | Gilkerson et al. |
| 2008/0071168 | A1 | 3/2008 | Gauglitz et al. |

*Primary Examiner* — Scott Getzow
(74) *Attorney, Agent, or Firm* — Pauly, DeVries Smith & Deffner, L.L.C.

(57) ABSTRACT

In one aspect a system includes an external communication device configured to interrogate a pulse generator, an external programmer device communicatively coupled to the external communication device; the external programmer device configured to receive a listing of valid electrode pairs from the pulse generator through the external communication device, the external programmer device configured to prevent a pacing, sensing, or shocking vector from being programmed by the user if a pair of electrodes needed for the vector are not included within the listing of valid electrode pairs. In another aspect a system includes an implantable medical device configured to detect the presence or absence of electrodes on an implanted stimulation lead coupled to the implantable medical device and to generate a valid electrode pair listing and compare the programmed electrode pairs with the valid electrode pair listing. Other embodiments are also included herein.

16 Claims, 10 Drawing Sheets

VECTOR CONFIGURATION DETECTION AND CORRECTIVE RESPONSE SYSTEMS AND METHODS

This application is a continuation of U.S. application Ser. No. 12/333,165, filed Dec. 11, 2008, which claims the benefit of U.S. Provisional Application No. 61/007,836, filed Dec. 14, 2007, the contents of all of which are herein incorporated by reference.

TECHNICAL FIELD

This application relates to the field of medical devices, and more specifically to systems and methods of detecting valid vector configurations and taking actions in response to the same.

BACKGROUND

Implantable medical devices are commonly used to treat patients with various conditions of the heart including life threatening tachycardia and various types of bradycardia. As an example of such devices, implantable cardiac rhythm management (CRM) systems generally include pulse generators and stimulation leads, and have electrodes implanted in or about the heart. Such devices typically function by administering pulses of electrical energy to the heart through the electrodes.

Many early CRM devices included a single electrode on the stimulation lead and electrical stimulation was delivered by passing a current from the pulse generator, through the stimulation lead, through the single electrode on the stimulation lead, into the patient's cardiac tissue, and back to the housing of the pulse generator to complete the circuit. Thus, the electrode on the stimulation lead served as one pole and the housing of the pulse generator itself served as the second pole. This type configuration, where the housing of the pulse generator serves as one pole, is generally known as a unipolar configuration.

Systems were also developed that included two electrodes on the stimulation lead. This allowed for the administration of electrical stimulation with one electrode of the stimulation lead serving as the first pole and the other electrode of the stimulation lead serving as the second pole. This type of configuration is known as a bipolar configuration.

Over time, stimulation leads have been developed having more than two electrodes. For example, some stimulation leads designed for use with CRM systems can include a first shocking coil in addition to a second shocking coil, along with a tip electrode and ring electrode, thus having four electrodes in total. In addition, stimulation leads designed for use with neurological stimulation systems have included four or more electrodes.

However, delivering a pulse of electrical stimulation only requires the use of two poles. As such, with many modern stimulation leads many different combinations of electrodes can be used in order administer electrical stimulation. The particular combination of electrodes used to deliver electrical stimulation can also be referred to as the "vector" because those electrodes determine the starting point and the ending point for electrical current moving through the patient's tissue. Generally, the clinician must choose which vector should be used by the device for purposes of sensing, pacing, and/or shocking. The clinician can input their choice into an external programmer device, such as a programmer/recorder/monitor device, which can in turn interface with implanted device and program it to use the desired vector.

SUMMARY

Embodiments included herein relate to systems and methods of automatically detecting valid vector configurations and taking corrective actions in response to invalid vector configurations. In an embodiment the invention includes a medical system including an external communication device configured to interrogate a pulse generator, the pulse generator coupled to one or more stimulation leads; an external programmer device communicatively coupled to the external communication device; and a user interface communicatively coupled to the external programmer device, the user interface configured to display information to a user; the external programmer device configured to receive a listing of valid electrode pairs from the pulse generator through the external communication device, the external programmer device configured to prevent a pacing, sensing, or shocking vector from being programmed by the user if a pair of electrodes needed for the vector are not included within the listing of valid electrode pairs.

In an embodiment, the invention includes a medical system including an implantable pulse generator coupled to one or more stimulation leads; an external communication device configured to interrogate the implantable pulse generator; an external programmer device communicatively coupled to the external communication device; and a user interface communicatively coupled to the external programmer device, the user interface configured to display information to a user; the external programmer device configured to receive a listing of valid electrode pairs from the pulse generator through the external communication device, the external programmer device configured to prevent a pacing, sensing, or shocking vector from being programmed by the user if a pair of electrodes needed for the vector are not included within the listing of valid electrode pairs.

In an embodiment, the invention includes a medical system including an implantable medical device configured to detect the presence or absence of electrodes on an implanted stimulation lead coupled to the implantable medical device and to generate a valid electrode pair listing by delivering a series of sub-threshold pulses of current and measuring impedance and determining if the measured impedance falls within a predefined range of impedance values; the implantable medical device comprising a telemetry circuit configured to receive programming instructions from an external device, the programming instructions including one or more programmed electrode pairs to be used for sensing, pacing, and/or shocking; the implantable medical device configured to compare the programmed electrode pairs with the valid electrode pair listing and to execute a corrective action procedure if one or more of the programmed electrode pairs are not included within the valid electrode pair listing.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION

As described above, stimulation leads have been developed having two or more electrodes. These multi-polar stimulation leads can be advantageous because they allow a clinician to choose the best combination of electrodes (best stimulation vector) from which to deliver electrical stimulation. Having this flexibility effectively allows the clinician to customize the system to the individual patient. For example, in the case of stimulation leads designed to be disposed within the coronary venous system, the stimulation lead may include multiple ring electrodes and the clinician can test different vectors (combinations of electrodes) in order to determine the one that is most effective for the individual patient.

However, along with increased flexibility sometimes also comes increased complication. For example, with multiple electrodes, the clinician must take this into consideration when the clinician is programming a patient's implanted device. This is because a problem can arise if the clinician programs the pulse generator to use a certain pacing, sensing, or shock vector that involves the use of an electrode that is not present or that is for some reason not operational.

Embodiments of the present system can help to prevent and/or correct such problems. In some embodiments, the system can automatically detect the number of operational (or valid) electrodes on a stimulation lead in order to reduce possible confusion during device programming. In some embodiments, the system can use information regarding the number of operational electrodes on a stimulation lead in order to alert, lock out, or otherwise inhibit or prevent the clinician from programming vectors that require an electrode that is actually missing or non-operational.

Figure 1:
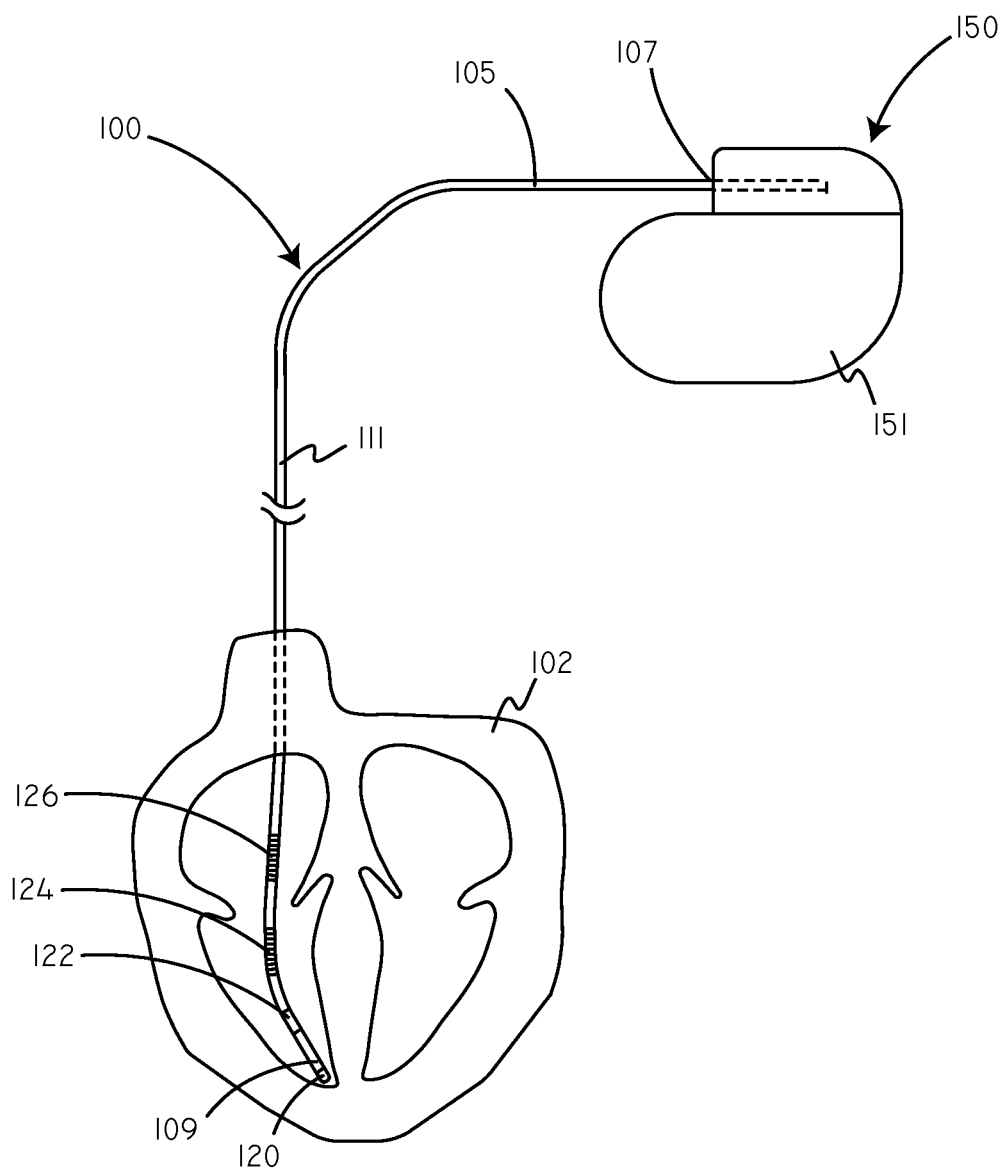
FIG. 1 is a schematic diagram of a lead and pulse generator in accordance with an embodiment.

Referring now to FIG. 1, a schematic view is shown of a multi-polar lead 100 coupled to a pulse generator 150. In some embodiments, the lead 100 is adapted to deliver pacing pulses of electrical current to a patient's heart 102. In some embodiments, the lead 100 is adapted to deliver cardioversion and/or defibrillation shocks to a patient's heart 102. Pulse generator 150 can be implanted in a surgically-formed pocket in the patient's chest or other desired location. Pulse generator 150 generally includes electronic components to perform signal analysis, processing, and control. Pulse generator 150 can include a power supply such as a battery, a capacitor, and other components housed in a case or can 151. The device can include microprocessors to provide processing and evaluation to determine and deliver electrical shocks and pulses of different energy levels and timing for ventricular defibrillation, cardioversion, and pacing to the heart 102 in response to cardiac arrhythmia including fibrillation, tachycardia, and/or bradycardia.

In one embodiment, lead 100 includes a lead body 105 extending from a proximal end 107 to a distal end 109 and having an intermediate portion 111. In this example, lead 100 includes one or more conductors (not shown), such as coiled conductors or other conductors, to conduct energy from pulse generator 150 to one or more electrodes, such as tip electrode 120, ring electrode 122, distal shocking coil electrode 124 and proximal shocking coil electrode 126. The conductors can also receive signals from the heart to transfer back to the pulse generator. The system can be configured as a unipolar system with the case acting as an electrode or a bipolar system with the electrical stimulation passing between two distally located electrodes, such as tip electrode 120 and ring electrode 122, for example. Leads used in conjunction with embodiments herein may have a plurality of electrodes, such as between 1 and 30 electrodes, for example. As such, in a bipolar pacing mode, many different electrode pairs can potentially be selected for use.

In various embodiments, the electronic components within the pulse generator 150 can be configured to automatically detect lead polarity (e.g., detect the number of electrodes on the stimulation lead). For example, the electronic components within the pulse generator can include impedance detection circuitry for evaluating the impedance between pairs of electrodes that may be present. Impedance detection may be performed in various ways. In an embodiment, sub-threshold excitation pulses are delivered between pairs of electrodes and the voltage is monitored in order to derive impedance. Availability of a pair of electrodes is indicated if the impedance between a pair of electrodes is within a predetermined range of impedance values. Impedance above or below this predetermined range would indicate that the particular pair of electrodes is not available (invalid) for delivery of electrical stimulation and/or sensing.

It will be appreciated that there are many different methods which can be used to determine impedance. By way of example, methods of determining impedance can include the Bridge method, the Resonant method, the I-V method, the RF I-V method, the Network analysis method, the Auto-balancing bridge method, and the like. In some embodiments, impedance is calculated using the I-V method. In a particular embodiment, an AC current pulse is applied across a lead vector (representing a particular pair of electrodes) and the resulting AC voltage is measured. The AC current pulse can be a sub-threshold excitable pulse of current. The impedance is then calculated according to the following equation:

$$z_x = \frac{V}{I}$$

After impedance is calculated for a particular pair of possible electrodes, the pair is determined to be functional or non-functional by comparing the measured impedance against a predetermined impedance range. In some embodiments, a series of impedance measurements for a particular pair of possible electrodes are made and then the average value is compared against a predetermined impedance range.

The precise range of acceptable impedances can depend on the particular combination of electrodes being tested and the type of electrode being tested. However, for example, an electrode pair for pacing may have a range of impedance of between 200 and 2500 Ohms. An electrode pair for defibrillation may have a range of impedance of between 200 and 2000 Ohms.

After impedance is measured and the functionality is assessed for a first possible electrode pair (or vector), impedance and functionality can then be assessed for other possible combinations of electrodes. In some embodiments, assessment of electrode pairs can start with a particular chamber of the heart and then move on to other chambers. For example, the system can start with the right atrium and check impedance between all possible electrode combinations on the right atrial stimulation lead. If a right ventricular stimulation lead is present, then the device can move on to assess the impedance between all possible electrode combinations on the right ventricular lead. Similarly, if a left ventricular stimulation lead is present, the device can move on to assess the impedance between all possible electrode combinations on the left ventricular stimulation lead.

Figure 2:
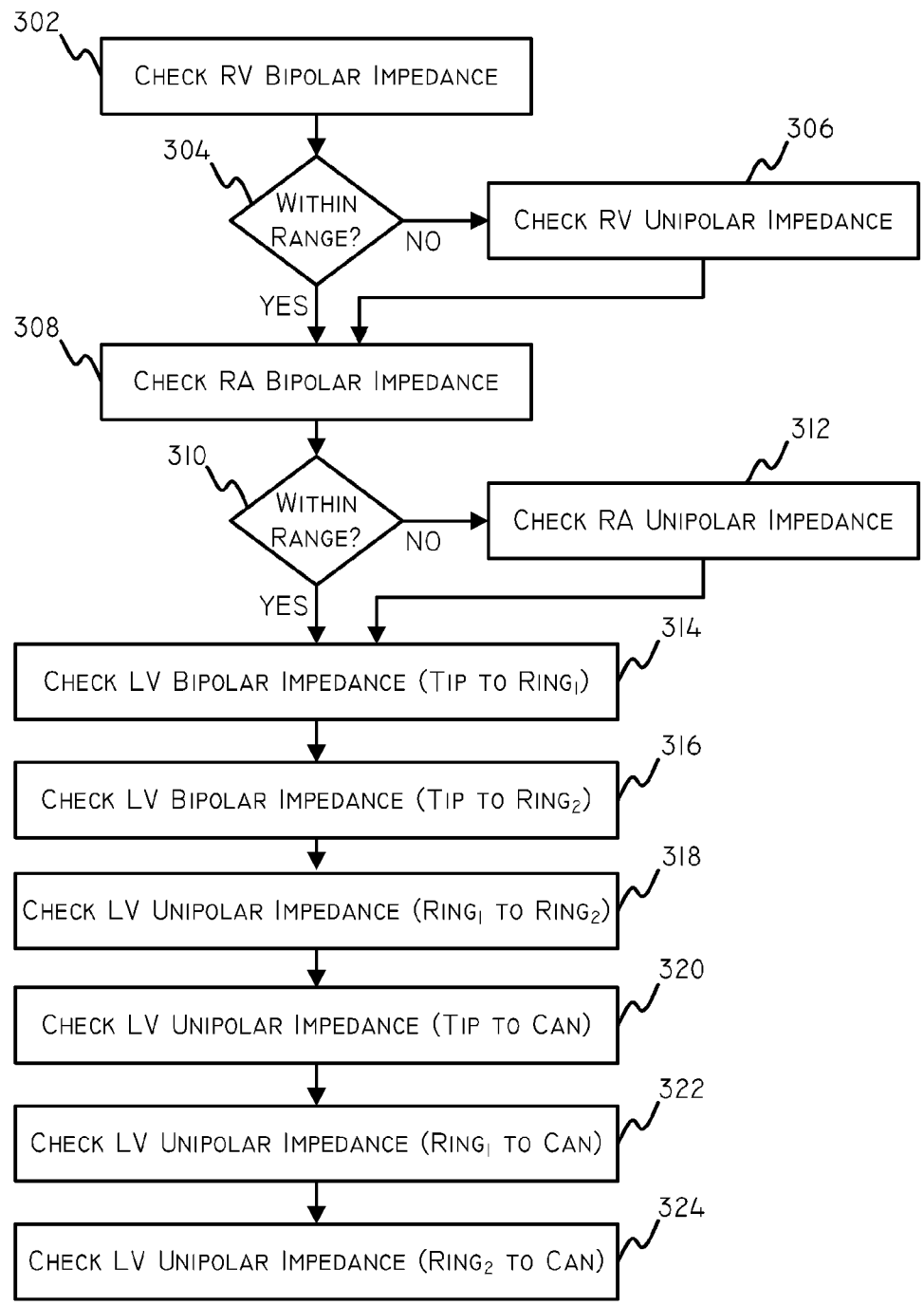
FIG. 2 is a flowchart illustrating a method for automatically checking valid electrode pairs in accordance with an embodiment.

Referring now to FIG. 2, a flowchart of an exemplary process of determining the polarity and functionality of stimulation leads is shown. In this embodiment, it is assumed that the right atrial stimulation lead and the right ventricular stimulation lead can have up to two electrodes (e.g., tip and ring). For the left ventricular stimulation lead, it is assumed that it can have up to three electrodes (tip, $ring_1$, and $ring_2$). However, it will be appreciated that embodiments of methods included herein, can be applied in the context of stimulation leads that have a number of electrodes exceeding two or three. For example, embodiments of methods included herein can be applied in the context of stimulation leads having 32 or more electrodes. Thus, it is not a requirement to make an assumption that the right atrial stimulation lead and the right ventricular stimulation lead can have, at most, two electrodes. Rather, this assumption is just made in this example for purposes of conciseness of illustration.

In many embodiments, the system can start by assuming that every electrode that the particular implanted pulse generator could possibly work with is operational and can then serially test all of them, or a subset of them, in order to determine which electrodes are actually operational. For example, if the particular pulse generator used is capable of utilizing three different electrodes on a particular stimulation lead, then the system can start impedance testing with the assumption that three different electrodes may be present and need to be tested for the particular stimulation lead. In some embodiments the system can start impedance testing with the assumption that the following nine electrodes may be present and need to be tested: can, lv-distal, lv-proximal, a-tip, a-ring, v-tip, v-ring, v-distal, and v-proximal.

In a first operation 302, the system can check the right ventricle (RV) bipolar impedance. That is, the system can determine the impedance as measured between two electrodes that may be on the right ventricular stimulation lead. Then the system can determine whether or not the impedance as measured is within a predetermined range in a second operation 304.

If the impedance is not within the predetermined range, then this means that at least one of the electrodes is not operational, and the system can go on to determine the RV unipolar impedance in a third operation 306. That is, the system can determine the impedance as measured between an electrode (such as the tip electrode) on the RV stimulation lead and the housing of the implanted device (the housing serving as a second electrode-unipolar). The system can then check the unipolar impedance in this manner for the other electrode (such as the ring electrode) assumed to be present.

However, if the impedance is within the predetermined range, then this can be taken to mean that both electrodes assumed to be present on the right ventricular stimulation lead are operational and the system can then move on to a fourth operation 308 where the system can check the right atrium (RA) bipolar impedance. That is, the system can check the impedance between two electrodes that may exist on the right atrium stimulation lead. Then the system can determine whether or not the impedance as measured is within a predetermined range in a fifth operation 310.

If the impedance is not within the predetermined range, the system can determine the RA unipolar impedance in a sixth operation 312. That is, the system can determine the impedance as measured between an electrode (tip electrode) on the RA stimulation lead and the housing of the implanted device (the housing serving as a second electrode). The system can then check the unipolar impedance in this manner for the other electrode (such as the ring electrode) assumed to be present.

However, if the impedance is within the predetermined range, then it can be taken to mean that both electrodes on the RA stimulation lead are operational and the system can move on to a seventh operation 314 where the system can check the left ventricular (LV) bipolar impedance as measured between the tip electrode and a first ring electrode.

Next, the system can check the left ventricular (LV) bipolar impedance as measured between the tip electrode and a second ring electrode in an eighth operation 316.

Next, the system can check the left ventricular (LV) bipolar impedance as measured between the first ring electrode and the second ring electrode in a ninth operation 318.

Next, the system can check the left ventricular (LV) unipolar impedance as measured between the tip electrode and the pulse generator housing ("can") in a tenth operation 320.

Next, the system can check the left ventricular (LV) unipolar impedance as measured between the first ring electrode and the pulse generator housing in an eleventh operation 322.

Next, the system can check the left ventricular (LV) unipolar impedance as measured between the second ring electrode and the pulse generator housing in a twelfth operation 324.

It will be appreciated that the operations shown in FIG. 2 may be performed in a different order while still falling within the scope of that included herein. In addition, in some embodiments different specific impedance checks can be omitted or added depending on the configuration of the particular device performing the impedance checks and user preferences. As such, the series of steps in FIG. 2 are just provided by way of illustration.

Systems in accordance with embodiments herein can initiate the process of determining the polarity and functionality of stimulation leads in various ways. For example, the system can be configured so that the process of determining the polarity and functionality of stimulation leads is initiated in response to a triggering event or at a given time interval. In some embodiments, the system can be configured so that the process of determining the polarity and functionality of stimulation leads is initiated every time a stimulation lead is coupled to a pulse generator. In some embodiments, the system can be configured so that the process of determining the polarity and functionality of stimulation leads is initiated based on an initiation signal received from an external device, such as from an external programmer device. In some embodiments, the system can be configured so that the process of determining the polarity and functionality of stimulation leads is initiated if a previously programmed valid electrode pair becomes invalid. In some embodiments, the system can be configured so that the process of determining the polarity and functionality of stimulation leads is initiated every second, every thirty seconds, every thirty minutes, or at another fixed time interval.

In some embodiments, information regarding the number of operational electrodes on each stimulation lead can be determined automatically such as through the methods described above. However, in other embodiments, information regarding the number of electrodes on each stimulation lead can be previously programmed into the device and stored for future use. For example, a clinician may manually perform various diagnostic procedures in order to determine the number of operational electrodes on each lead and then program this information into the system. As another example, information regarding the number of electrodes on each lead may be programmed into the system at the time of implantation following physical inspection of the actual stimulation leads to be implanted. As such, it will be appreciated that there are various approaches by with the system can acquire information regarding the number of operational electrodes on each stimulation lead.

After the number of operational electrodes on each stimulation lead is known the system can take appropriate corrective action if attempts are made to program the system in ways that would require the use of an electrode that has been found to be missing or otherwise not operational. In various embodiments, such appropriate corrective action can include providing alerts, fault warnings, reverting back to programming utilizing a verified electrode pair, or locking out or otherwise inhibiting or preventing the clinician from programming vectors requiring an electrode that is actually missing. In various embodiments, corrective actions can be taken at the level of the implanted device, at the level of the external programmer device, or both.

Figure 3:
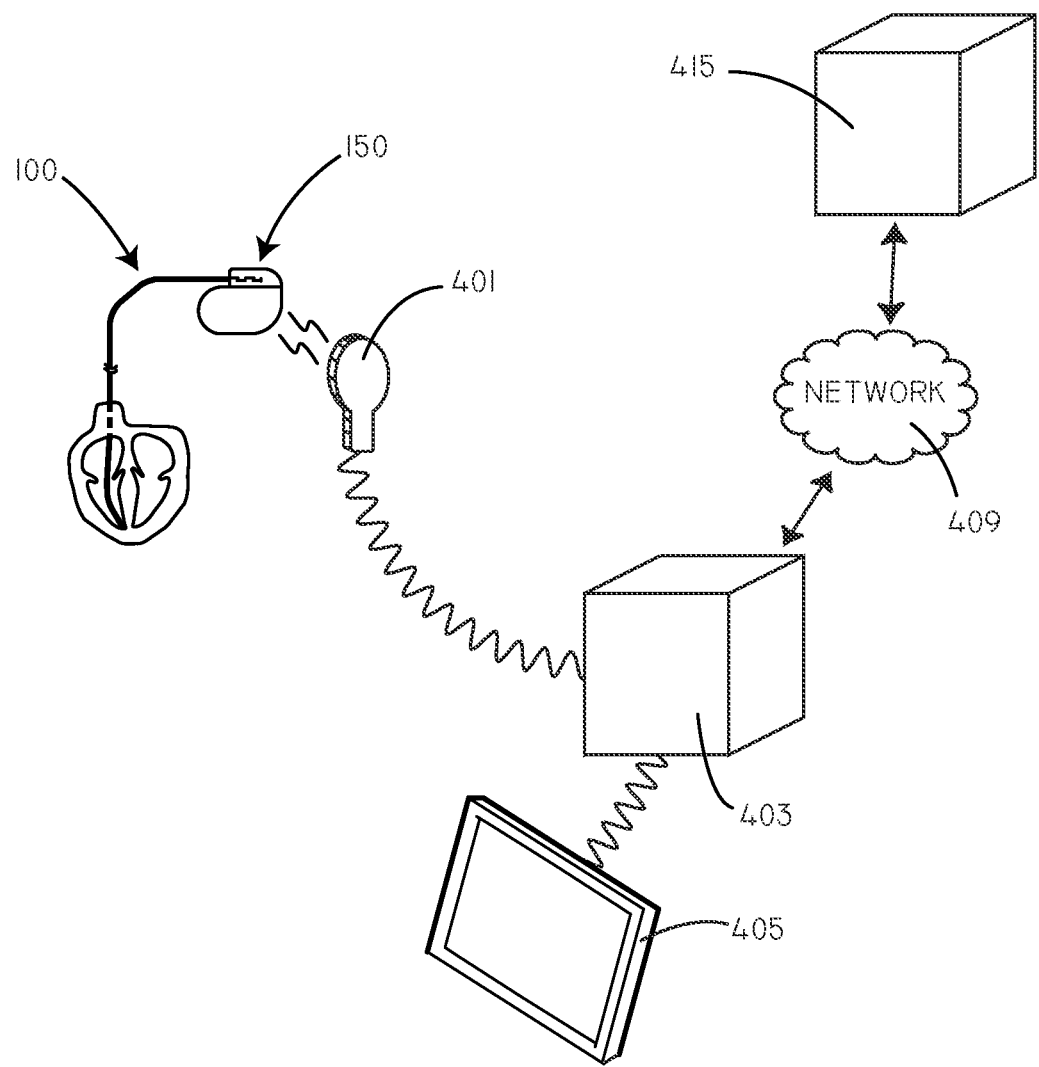
FIG. 3 is a schematic diagram of a system in accordance with an embodiment.

FIG. 3 shows a system in accordance with an embodiment. The system includes an external communication device, such as a wireless telemetry device 401 or interrogation wand, to interrogate pulse generator 150 which has one or more leads 100 attached to the pulse generator. The telemetry device 401 can ascertain the number of electrodes on the lead by interrogating the pulse generator 150, which may have already determined the number of operational electrodes on each stimulation lead in accordance with methods described herein or other methods, can determine the number of operational electrodes in response to an initiation signal received during the interrogation, or has had information regarding operational leads programmed into it previously. The system also includes a programmer device 403, such as a computer, communicatively coupled to the telemetry device 401, and a user interface 405, such as including a video output, communicatively coupled to the programmer device 403.

The user interface 405 displays information to a user depending on the interrogation by the telemetry device 401. For example, the user interface can display different shock, pacing, or sensing vectors (pairs of electrodes) selectable by the physician or other user. In one embodiment, the programmer device 403 is programmed to deny an inappropriate pacing, sensing, or shocking vector from being programmed if the electrodes needed for the vector are not found on the lead. For example, the inappropriate vector can either be absent (not displayed) from the screen of the user interface, or the inappropriate vector can be made unselectable, such as through graying-out or similar methods. In other embodiments, a warning notification can be displayed. In some embodiments, the warning notification can include information regarding alternative electrode pairs.

In one embodiment, the programmer device 403 can be programmed such that if the physician selects an inappropriate vector, the programmer device 403 automatically selects a different, usable vector. The programmer device can also be configured to locally or remotely alert the user of the inappropriate vector or of the automatically substituted vector.

In one embodiment, the programmer device 403 can further be communicatively coupled to a network 409 and a remote device 415. This configuration allows for local or remote programming of the pulse generator 150, local or remote alerting of the user, and allow for any alert not only to notify the user of an inappropriate vector, but also to notify the user of the automatically-substituted vector.

In another example, the pulse generator 150 is also programmed to deliver a fault warning if an inappropriate pacing, sensing, or shocking vector is attempted. For example, the fault warning can be stored in the device's memory.

Figure 4:
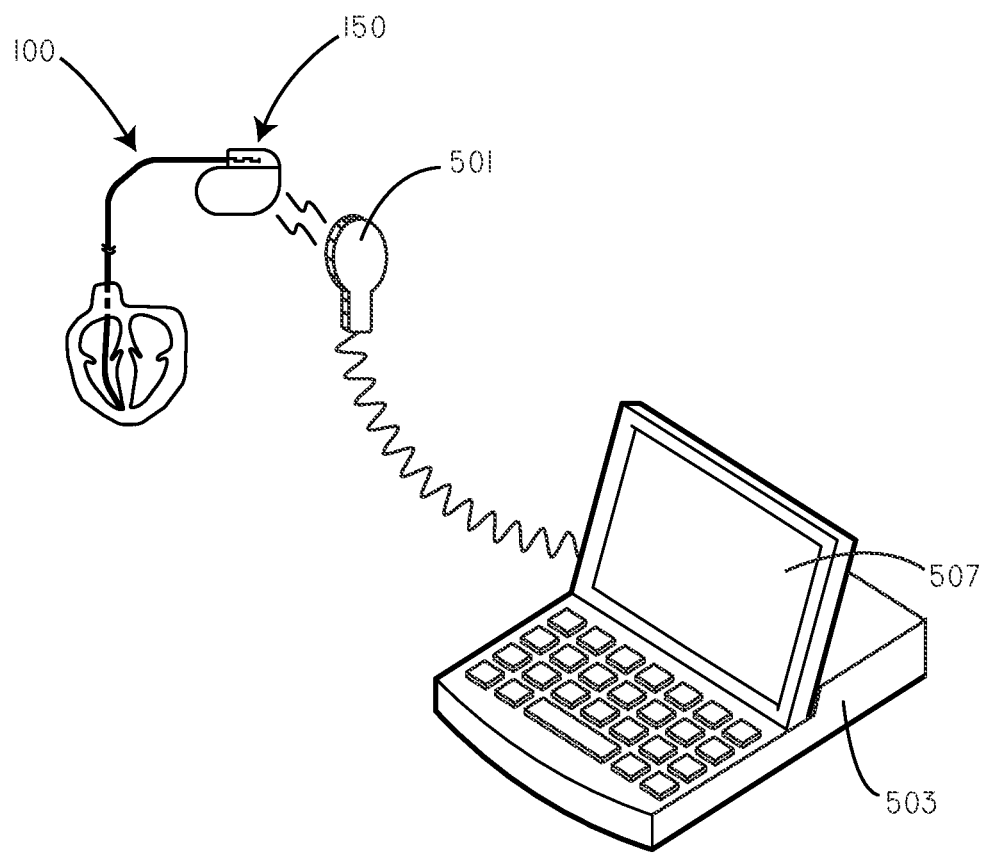
FIG. 4 is a schematic diagram of a system in accordance with another embodiment.

It will be appreciated that the components of the system can take on various forms. For example, in an embodiment, the programmer device and the user interface can be part of an integral unit, such as in the case of a programmer/recorder/monitor (PRM) device. Referring now to FIG. 4, a schematic view of a system is shown in accordance with another embodiment of the invention. The system includes an external communication device 501. The system also includes an external programmer device, such as PRM 503, which includes a user interface 507. The system can be configured to interrogate an implanted device 150 coupled to stimulation leads 100.

Figure 5:
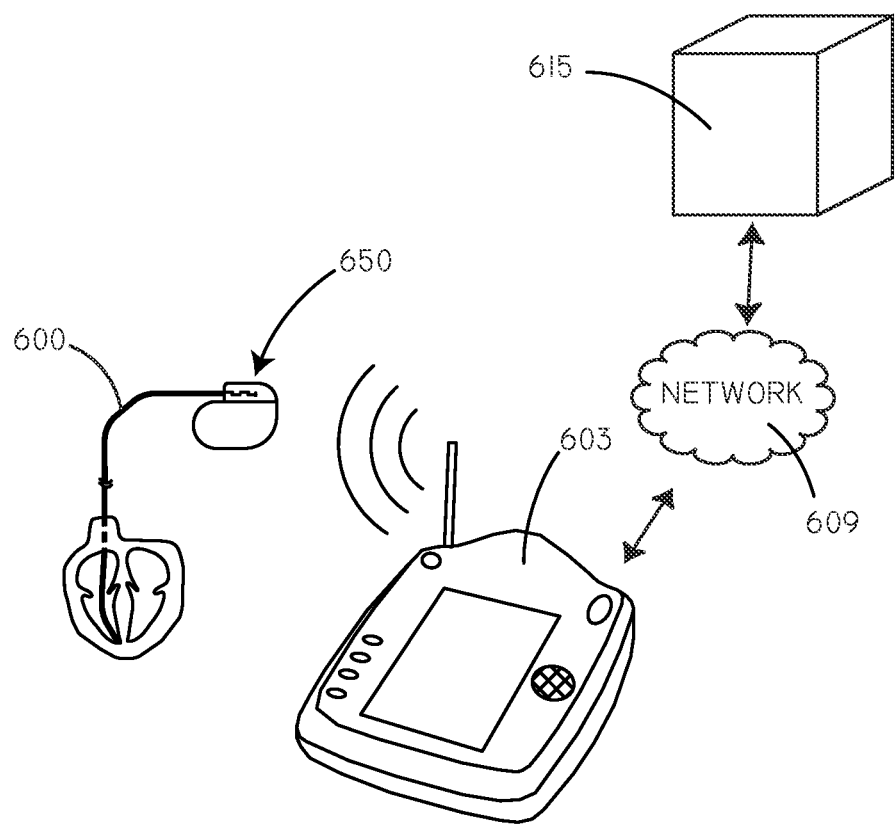
FIG. 5 is a schematic diagram of a system in accordance with another embodiment.

In some embodiments, the components of the system can include an in-home monitoring device. Referring now to FIG. 5, a schematic view of a system is shown in accordance with another embodiment of the invention. In this embodiment, the external communication device, the external programmer device, and the user interface are integrated into an in-home monitoring device 603. The in-home monitoring device 603 can communicate with a remote system 615 through a communications network 609. The system can be configured to interrogate an implanted device 650 coupled to stimulation leads 600.

Figure 6:
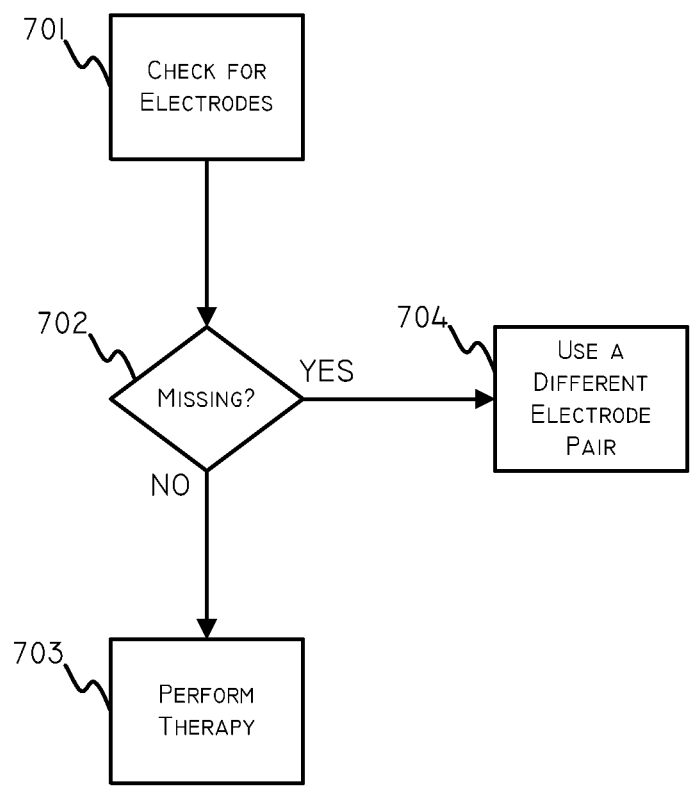
FIG. 6 is a flow chart of a method in accordance with an embodiment.

FIG. 6 shows a method according to one embodiment of the present system. In this method, the pulse generator is programmed to detect the presence or absence of electrodes on one or more leads in a first operation 701. The system can then determine whether or not, based on the electrodes that have been determined to be present, the programming calls for electrodes that are not in fact present or operational in a second operation 702. If the programming calls for electrodes that are not present or operational, then the system can be programmed to utilize an alternative pacing, sensing, or shocking vector (alternative pair of electrodes) in a third operation 704. However, if the proper electrodes are present, then therapy can be delivered using the originally programmed vector in a fourth operation 703.

Figure 7:
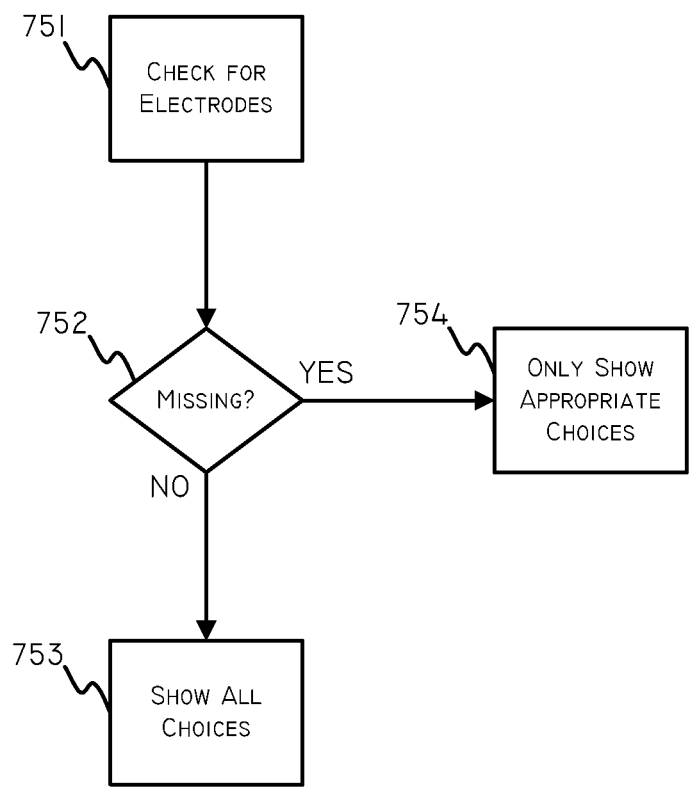
FIG. 7 is a flow chart of a method in accordance with another embodiment.

FIG. 7 shows a method according to another embodiment. This method can support programming of an implanted device either before or after implantation. In this method, the pulse generator is programmed to detect the presence or absence of electrodes on a lead in a first operation 751. The system can then determine whether or not, based on the electrodes that have been determined to be present, the programming calls for electrodes that are not in fact present or operational in a second operation 752. If the programming calls for electrodes that are not present or operational, then the system can be configured in a third operation 754 to only show programming choices through the user interface that will work with the particular electrodes present. However, if the proper electrodes are present, then in a fourth operation 753, the system can be configured to show all programming choices through the user interface.

Figure 8:
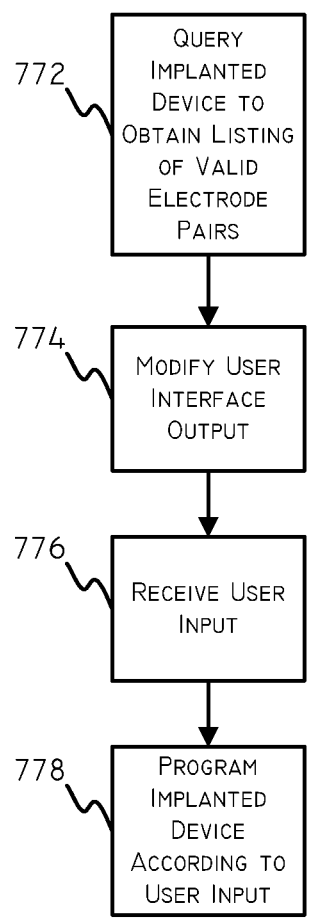
FIG. 8 is a flow chart of a method in accordance with another embodiment.

FIG. 8 shows a flowchart in accordance with another embodiment. In a first operation 772, an external device, such as an external programmer device, can query an implanted device to obtain a listing of valid electrode pairs. Depending on the listing of valid electrode pairs received from the implanted device, a user interface can be modified in a second operation 774. For example, programming options requiring a pair of electrodes not included within the listing of valid electrode pairs can be prevented from being selected. For example, in some embodiments, the user interface can be modified so that programming options requiring invalid electrode pairs are not displayed through the user interface output. In some embodiments, the user interface can be modified so that programming options requiring invalid electrode pairs are made unselectable, such as by graying them out. In such ways, the user interface can be modified in some embodiments so that a system user is prevented in the first instance from selecting programming options requiring an invalid electrode pair. Then, in a third operation 776, the system can receive user input. Finally, in a fourth operation 778, the system can program the implanted device according to the user input.

Figure 9:
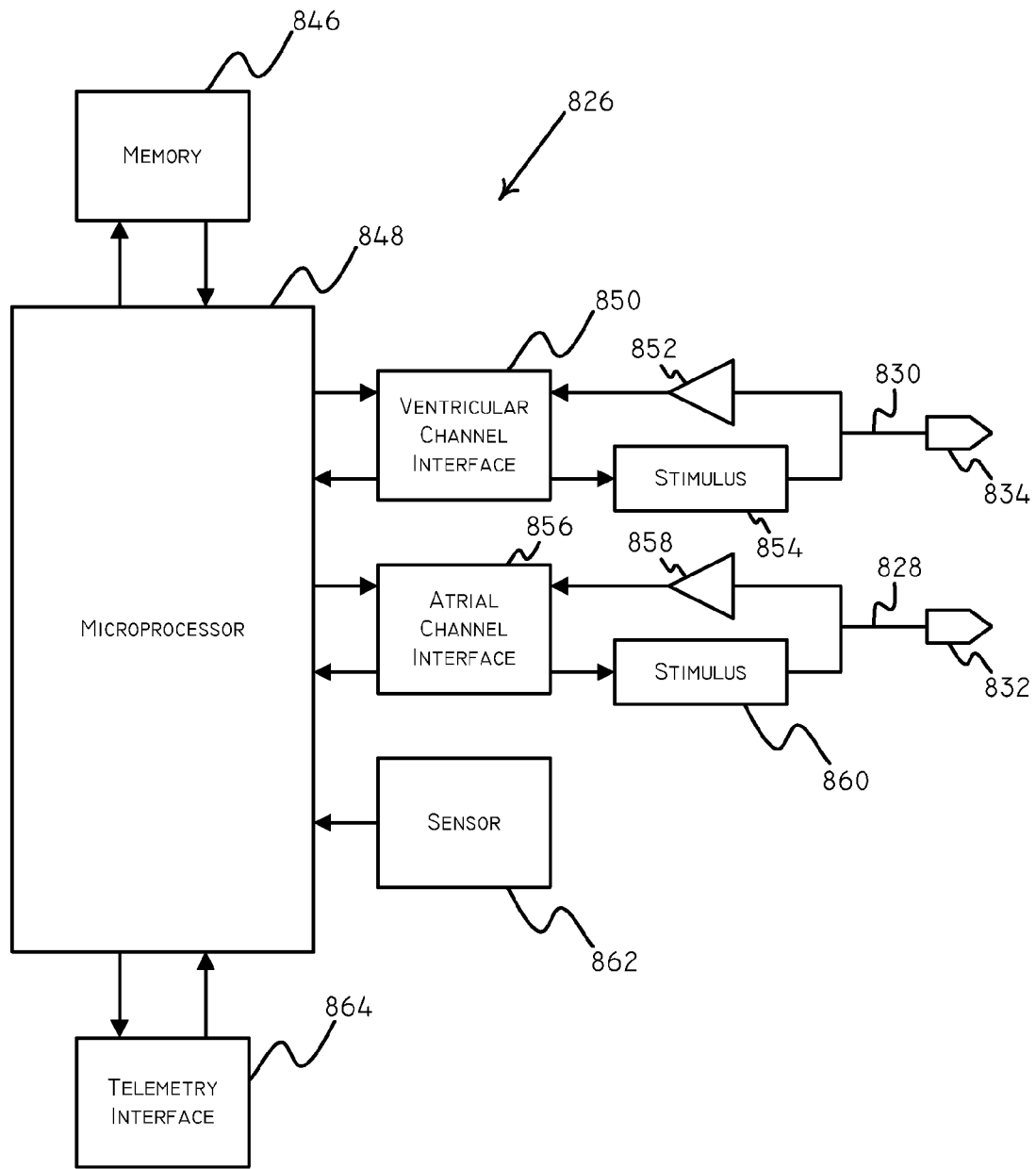
FIG. 9 is a schematic diagram of components of an implantable medical device in accordance with some embodiments.

Referring now to FIG. 9, a schematic view is shown of various components of an implanted device in accordance with various embodiments herein. The implanted device 826 can include a microprocessor 848. The microprocessor 848 can execute instructions and can communicate with a memory 846 via a bidirectional data bus. The memory 846 typically comprises ROM or RAM for program storage and RAM for data storage.

In this embodiment, the device can include one or more ventricular sensing and pacing channels including sensing amplifier 852, output circuit 854, and ventricular channel interface 850, which can be in communication with electrode 834 and stimulation lead 830. In various embodiments herein, multiple electrodes can be in communication with the ventricular sensing and pacing channels, though only electrode 834 is shown in this view.

In this embodiment, the device can also include one or more atrial sensing and pacing channels including sensing amplifier 858, output circuit 860, and an atrial channel interface 856, which can be in communication with electrode 832 and stimulation lead 828. In various embodiments herein, multiple electrodes can be in communication with the atrial sensing and pacing channels, though only electrode 832 is shown in this view. Both the ventricular sensing and pacing channels and the atrial sensing and pacing channels can communicate bidirectionally with a port of microprocessor 848.

It will be appreciated that in various embodiments devices can include other sensing and pacing channels such as a second ventricular sensing and pacing channel to accommodate both right and left ventricular pacing. In addition, in various embodiments, devices can also include a separate shocking channel for delivering defibrillation and/or cardioversion shocks.

The channel interfaces 850 and 856 can include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. In some embodiments, the device 826 can also include one or more sensors 862, such as an accelerometer, a posture sensor, an impedance sensor, a minute ventilation sensor, a pressure sensor, or the like. The device 826 can also include a telemetry module 864 for communicating with an external interface device. The device 826 can be configured to execute various methods as described herein. For example, the device 826 can be configured to determine valid electrode pairs through measurements of impedance.

Figure 10:
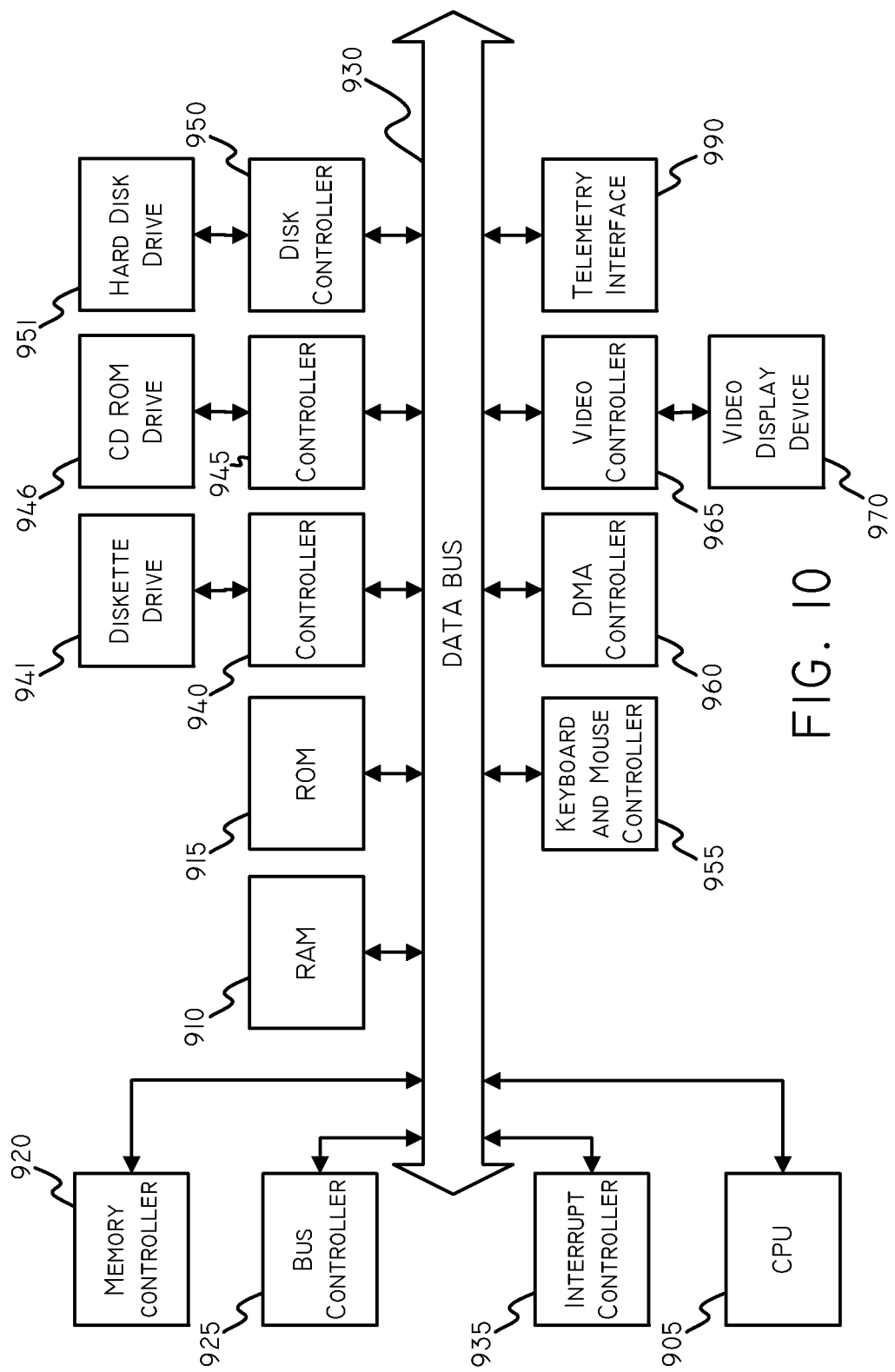
FIG. 10 is a schematic diagram of components of an external programmer device in accordance with some embodiments.

External programmer devices included with various embodiments herein, such as programmer/recorder/monitors, can include components common to many types of computing devices. Referring now to FIG. 10, a diagram of various components of a programmer device is shown in accordance with some embodiments of the invention. However, it will be appreciated that this is just one example. The programmer device includes a central processing unit (CPU) 905 or processor, which may include a conventional microprocessor, random access memory (RAM) 910 for temporary storage of information, and read only memory (ROM) 915 for permanent storage of information. A memory controller 920 is provided for controlling system RAM 910. A bus controller 925 is provided for controlling data bus 930, and an interrupt controller 935 can be used for receiving and processing various interrupt signals from the other system components.

Mass storage can be provided by diskette drive 941, which is connected to bus 930 by controller 940, CD-ROM drive 946, which is connected to bus 930 by controller 945, and hard disk drive 951, which is connected to bus 930 by controller 950. User input to the programmer system may be provided by a number of devices. For example, a keyboard and mouse can connected to bus 930 by keyboard and mouse controller 955. DMA controller 960 is provided for performing direct memory access to system RAM 910. A user interface is generated by a video controller 965 or video output, which controls video display 970. The external system can also include a telemetry interface 990 or telemetry circuit which allows the external system to interface and exchange data with an implantable medical device. It will be appreciated that some embodiments of programmer may omit various elements shown in FIG. 10, while other embodiments may include elements not shown in FIG. 10.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. A medical system comprising:
   an external programmer device configured to initiate interrogation of a pulse generator, the pulse generator coupled to one or more stimulation leads; and
   a user interface communicatively coupled to the external programmer device, the user interface configured to display information to a user;
   the external programmer device configured to receive a listing of valid electrode pairs from the pulse generator, the external programmer device configured to display a notification through the user interface if the user attempts to program a pacing, sensing, or shocking vector that requires a pair of electrodes that is not found on the listing of valid electrode pairs, the notification including information regarding an alternative pacing, sensing, or shocking vector that may be substituted for the pacing, sensing, or shocking vector attempted by the user.

2. The medical system of claim 1, the external programmer device configured to make unselectable those programming options that require the use of a pair of electrodes not included within the listing of valid electrode pairs.

3. The medical system of claim 1, wherein the valid electrode pair listing is grouped by chambers of the heart.

4. The medical system of claim 3, wherein the information regarding an alternative pacing, sensing, or shocking vector that may be substituted for the pacing, sensing, or shocking vector attempted by the user regards an electrode pair from the valid electrode pair listing from the same heart chamber grouping as the attempted pair of electrodes.

5. The medical system of claim 1, the external programmer device configured to omit programming options from the user interface that would require the use of a pair of electrodes not included within the listing of valid electrode pairs.

6. A medical system comprising:
   an external programmer device configured to initiate interrogation of a pulse generator, the pulse generator coupled to one or more stimulation leads; and
   a user interface communicatively coupled to the external programmer device, the user interface configured to display information to a user;
   the external programmer device configured to receive a listing of valid electrode pairs from the pulse generator, the external programmer device configured to automatically select an alternative vector if the user attempts to program a pacing, sensing, or shocking vector that requires a pair of electrodes that is not included within the listing of valid electrode pairs.

7. The medical system of claim 6, the external programmer device configured to make unselectable those programming options that require the use of a pair of electrodes not included within the listing of valid electrode pairs.

8. The medical system of claim 6, wherein the valid electrode pair listing is grouped by chambers of the heart.

9. The medical system of claim 8, wherein the information regarding an alternative pacing, sensing, or shocking vector that may be substituted for the pacing, sensing, or shocking vector attempted by the user regards an electrode pair from the valid electrode pair listing from the same heart chamber grouping as the attempted pair of electrodes.

10. The medical system of claim 6, the external programmer device configured to omit programming options from the user interface that would require the use of a pair of electrodes not included within the listing of valid electrode pairs.

11. A method for vector configuration detection and corrective response comprising:
   initiating interrogation of an implanted pulse generator from an external programmer device;
   receiving a listing of valid electrode pairs from the pulse generator;
   displaying a notification through a user interface associated with the external programmer device if a system user attempts to program a pacing, sensing, or shocking vector that requires a pair of electrodes that is not found on the listing of valid electrode pairs, the notification including information regarding an alternative pacing, sensing, or shocking vector that may be substituted for the pacing, sensing, or shocking vector attempted by the user.

12. The method of claim 11, further comprising grouping the listing of valid electrode pairs by chamber of the heart.

13. The method of claim 11, further comprising making programming options that require the use of a pair of electrodes not included within the listing of valid electrode pairs unselectable.

14. The method of claim 11, further comprising delivering a fault warning if a system user attempts to program a pacing, sensing, or shocking vector that requires a pair of electrodes that is not found on the listing of valid electrode pairs.

15. The method of claim 14, further comprising storing the fault warning in system memory.

16. The method of claim 11, further comprising sending a command through the external communication device to the pulse generator to regenerate the listing of valid electrode pairs.

* * * * *